(12) United States Patent
Englund

(10) Patent No.: US 9,143,702 B2
(45) Date of Patent: Sep. 22, 2015

(54) LENS-FREE PLANAR IMAGER USING AN OPTICAL RESONATOR

(71) Applicant: The Trustees of Columbia University in the City of New York, New York, NY (US)

(72) Inventor: Dirk R. Englund, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 17 days.

(21) Appl. No.: 14/150,380

(22) Filed: Jan. 8, 2014

(65) Prior Publication Data

US 2014/0160336 A1 Jun. 12, 2014

Related U.S. Application Data

(63) Continuation of application No. PCT/US2012/048833, filed on Jul. 30, 2012.

(60) Provisional application No. 61/513,826, filed on Aug. 1, 2011.

(51) Int. Cl.
*G01B 11/00* (2006.01)
*H04N 5/30* (2006.01)
(Continued)

(52) U.S. Cl.
CPC ............... *H04N 5/30* (2013.01); *G02B 27/58* (2013.01); *G01N 2021/391* (2013.01); *G02B 6/241* (2013.01); *G02B 6/30* (2013.01); *G02B 2006/1213* (2013.01)

(58) Field of Classification Search
CPC .. G02B 6/29335; G02B 17/004; G02B 27/58; G02B 2006/1213; G02B 6/241; G02B 6/30; G01J 1/047; G01N 21/7746; G01N 2021/391; H04N 5/30; H01S 5/1028; H01S 5/1032; H01S 5/1035
See application file for complete search history.

(56) References Cited

U.S. PATENT DOCUMENTS 4,717,255 A 1/1988 Ulbers
5,431,055 A 7/1995 Takata et al.
(Continued)

FOREIGN PATENT DOCUMENTS

EP 1 432 048 6/2004
WO WO 2010/141114 12/2010
(Continued)

OTHER PUBLICATIONS

U.S. Appl. No. 14/253,250, filed Apr. 15, 2014.
(Continued)

*Primary Examiner* — Tarifur Chowdhury
*Assistant Examiner* — Michael P Lapage
(74) *Attorney, Agent, or Firm* — Baker Botts L.L.P.

(57) ABSTRACT

Techniques for lens-free imaging using optical resonance, including providing a series of standing waves indexed by a wave vector to an optical resonator having a predetermined dispersion relation. The intensity of the wavelengths corresponding to the standing waves can be measured with a photodetector. A magnitude and shift of the wave vector corresponding to each of the standing waves can be determined, and spatial information in k-space can be determined from the magnitude and shift of the wave vector corresponding to each of the standing waves using an inversion relationship. A transform can be applied to the spatial information to generate an image.

15 Claims, 10 Drawing Sheets

(51) Int. Cl.
*G02B 27/58* (2006.01)
*G01N 21/39* (2006.01)
*G02B 6/30* (2006.01)
*G02B 6/24* (2006.01)
*G02B 6/12* (2006.01)

(56) References Cited

U.S. PATENT DOCUMENTS

| | | | |
|---|---|---|---|
| 5,455,421 A | 10/1995 | Spears | |
| 5,493,393 A | 2/1996 | Beranek et al. | |
| 5,565,987 A | 10/1996 | Jain et al. | |
| 5,760,939 A | 6/1998 | Nagarajan et al. | |
| 6,069,645 A | 5/2000 | Vincent | |
| 6,157,042 A | 12/2000 | Dodd | |
| 6,512,866 B1 | 1/2003 | Fan et al. | |
| 6,584,126 B2 | 6/2003 | Wang et al. | |
| 6,614,533 B1 | 9/2003 | Hata et al. | |
| 6,752,008 B1 | 6/2004 | Kley | |
| 7,091,500 B2 | 8/2006 | Schnitzer et al. | |
| 7,184,642 B2 | 2/2007 | Hoshi et al. | |
| 7,347,085 B2 | 3/2008 | Taber | |
| 7,356,225 B2 | 4/2008 | Loebel et al. | |
| 7,359,111 B1 | 4/2008 | Bratkovski | |
| 7,406,860 B2 | 8/2008 | Zhou et al. | |
| 7,474,811 B1 | 1/2009 | Quitoriano et al. | |
| 7,572,648 B2 | 8/2009 | Suzuki et al. | |
| 7,592,632 B2 | 9/2009 | Takagi | |
| 7,599,061 B1 | 10/2009 | Ting et al. | |
| 7,659,536 B2 | 2/2010 | Krishna et al. | |
| 7,817,274 B2 | 10/2010 | Zhang | |
| 8,053,782 B2 | 11/2011 | Avouris et al. | |
| 8,116,624 B1 | 2/2012 | Wach | |
| 8,189,302 B2 | 5/2012 | Gurney et al. | |
| 8,213,751 B1 | 7/2012 | Ho et al. | |
| 8,263,986 B2 | 9/2012 | Hajj-Hassan et al. | |
| 2001/0055147 A1 | 12/2001 | Little et al. | |
| 2002/0068018 A1* | 6/2002 | Pepper et al. | 422/82.05 |
| 2003/0020926 A1 | 1/2003 | Miron | |
| 2004/0067163 A1* | 4/2004 | Prasad et al. | 422/58 |
| 2004/0150873 A1 | 8/2004 | Pearsall | |
| 2004/0156610 A1 | 8/2004 | Charlton et al. | |
| 2004/0179803 A1 | 9/2004 | Bourelle | |
| 2005/0110992 A1 | 5/2005 | Scherer et al. | |
| 2005/0218328 A1 | 10/2005 | Suzuki et al. | |
| 2006/0058685 A1 | 3/2006 | Fomitchov et al. | |
| 2006/0188721 A1 | 8/2006 | Irvin et al. | |
| 2006/0283338 A1 | 12/2006 | Degertekin | |
| 2007/0020144 A1 | 1/2007 | Du et al. | |
| 2007/0107501 A1 | 5/2007 | Taber | |
| 2008/0089367 A1 | 4/2008 | Srinivasan et al. | |
| 2008/0159679 A1 | 7/2008 | Sigalas et al. | |
| 2008/0223119 A1 | 9/2008 | Phan et al. | |
| 2009/0015757 A1 | 1/2009 | Potts et al. | |
| 2009/0237666 A1 | 9/2009 | Vollmer et al. | |
| 2009/0273779 A1 | 11/2009 | Baumberg et al. | |
| 2010/0014077 A1 | 1/2010 | Khetani et al. | |
| 2010/0117647 A1 | 5/2010 | Madore | |
| 2010/0142569 A1 | 6/2010 | Magel | |
| 2010/0176200 A1 | 7/2010 | Vollmer et al. | |
| 2010/0202035 A1 | 8/2010 | Noh et al. | |
| 2010/0275334 A1 | 10/2010 | Proksch et al. | |
| 2011/0042650 A1 | 2/2011 | Avouris et al. | |
| 2011/0149296 A1 | 6/2011 | Tearney et al. | |
| 2011/0151602 A1 | 6/2011 | Speier | |
| 2011/0158268 A1 | 6/2011 | Song | |
| 2011/0175060 A1 | 7/2011 | Okai et al. | |
| 2011/0269259 A1 | 11/2011 | Tatani et al. | |
| 2011/0280263 A1 | 11/2011 | Kieu et al. | |
| 2012/0039344 A1 | 2/2012 | Kian et al. | |
| 2012/0044489 A1 | 2/2012 | Chakravarty et al. | |
| 2012/0045169 A1 | 2/2012 | Hu et al. | |
| 2012/0069338 A1 | 3/2012 | Afzali et al. | |
| 2012/0206726 A1* | 8/2012 | Pervez et al. | 356/402 |
| 2012/0219250 A1 | 8/2012 | Ren et al. | |
| 2012/0268745 A1 | 10/2012 | Kudenov et al. | |
| 2014/0196179 A1 | 7/2014 | Englund et al. | |
| 2014/0233028 A1 | 8/2014 | Englund et al. | |

FOREIGN PATENT DOCUMENTS

| | | |
|---|---|---|
| WO | WO 2011/046875 | 4/2011 |
| WO | WO 2011/089119 | 7/2011 |
| WO | WO 2012/115793 | 8/2012 |
| WO | WO 2012/128943 | 9/2012 |

OTHER PUBLICATIONS

U.S. Appl. No. 14/501,735, filed Sep. 30, 2014.
International Search Report and Written Opinion for PCT/US13/073613, dated May 30, 2014.
International Search Report and Written Opinion for PCT/US13/032373, dated Jun. 13, 2013.
International Search Report and Written Opinion for PCT/US13/052020, dated Dec. 20, 2013.
International Search Report and Written Opinion for PCT/US13/031736, dated Oct. 29, 2013.
International Search Report and Written Opinion for PCT/US12/048837, dated Dec. 27, 2012.
International Search Report and Written Opinion for PCT/US12/048833, dated Apr. 5, 2013.
International Search Report and Written Opinion for PCT/US12/061126, dated Jan. 10, 2013.
Andryieuski et al., "Nanocouplers for infrared and visible light", *Advances in OptoElectronics*, Retrieved from the Internet: URL:http://arxiv.org/ftp/arxiv/papers/1206/1206.6601.pdf (32 pages) (2012).
Ban et al., "Near-infrared to visible light optical upconversion by direct tandem integration of organic light-emitting diode and inorganic photodetector", *Applied Physics Letters*, 90:093108 (2007).
Bao et al., "Graphene photonics, plasmonics, and broadband optoelectronic devices", *ACS Nano*, 6(5):3677-3694 (2012).
Bonaccorso et al., "Graphene photonics and optoelectronics", *Nature Photonics*, 4:611-622 (2010).
Boriskina et al., "Spectrally engineered photonic molecules as optical sensors with enhanced sensitivity: a proposal and numerical analysis", *JOSA B*, 23(8):1565-1573 (2006).
Bullis, "Graphene Transistors", *MIT Technology Review*, (Jan. 28, 2008); Retrieved from http://www.technologyreview.com/news/409449/graphene-transistors/ [downloaded on Oct. 23, 2014].
Butler et al., Nomenclature, symbols, units and their usage in spectrochemical analysis-IX. Instrumentation for the spectral dispersion and isolation of optical radiation (IUPAC Recommendations 1995), *Pure and Applied Chemistry*, 67(10):1725-1744 (1995).
Craven-Jones et al., "Infrared hyperspectral imaging polarimeter using birefringent prisms", *Appl. Opt.*, 50(8):1170-1185 (2011).
DeCorby et al., "Chip-scale spectrometry based on tapered hollow Bragg waveguides", *Optics Express*, 17(19):16632-16645 (2009).
Fang et al., "Graphene-antenna sandwich photodetector", *Nano Letters*, 12(7):3808-3813 (2012).
Furchi et al., "Microactivity-integrated grapheme photodetector", *Nano Letters*, 12(6):2773-2777 (2012).
Gan et al., "A high-resolution spectrometer based on a compact planar two dimensional photonic crystal cavity array", *Applied Physics Letters*, 100:231104 (4 pages) (2012).
Geim et al., "The rise of grapheme", *Nature Materials*, 6(3):183-191 (2007).
Huang et al., "Study of residual background carriers in midinfrared in As/Ga Sb superlattices for uncooled detector operation", *Applied Physics Letters*, 92:071102 (2008).
Ismail et al., "Raman spectroscopy with an integrated arrayed-waveguide grating", *Optic Letters*, 36(23):4629-4631 (2011).
Jelezko et al., "Read-out of single spins by optical spectroscopy", *Journal of Physics: Condensed Matter*, 16:R1089-R1104 (2004).
Kim et al., "Graphene-based plasmonic waveguides for photonic integrated circuits", *Optics Express*, 19(24):24557-24562 (2011).

(56) References Cited

OTHER PUBLICATIONS

Kuzmenko et al., "Universal optical conductance of graphite", *Phys. Rev. Lett.*, 100(11):117401 (2008).

Lidstone et al., "Label-free imaging of cell attachment with photonic crystal enhanced microscopy", *Analyst*, 136(18):3608-3615 (2011).

Liu et al., "A graphene-based broadband optical modulator", *Nature*, 474(7349):64-67 (2011).

Lu et al., "Nanoscale graphene electro-optic modulators based on graphene-slot waveguides", *JOSA B*, 29(6):1490-1496 (2012).

Makhlouf et al., "Multispectral confocal microendoscope for in vivo and in situ imaging", *Journal of Biomedical Optics*, 13(4):044016 (2008).

Pisani et al., "Compact imaging spectrometer combining fourier transform spectroscopy with a Fabry-Perot interferometer", *Optics Express*, 17(10):8319-8331 (2009).

Sarkissian et al., "Spectroscopy of a tapered-fiber photonic crystal waveguide coupler", *Optics Express*, 17(13):10738-10747 (2009).

Sheilds et al., "A scanning cavity nanoscope", *41$^{st}$ Annual Meeting of the APS Division of Atomic Molecular and Optical Physics*, 55(5), Tuesday-Saturday, May 25-29, 2010, Houston, Texas.

Tsuji et al., "An efficient and compact difference-frequency-generation spectrometer and its application to $^{12}CH_3D/^{12}CH_4$ isotope ratio measurements", *Sensors (Basel)*, 10(7):6612-6622 (2010).

Wang et al., "Graphene on SiC as a Q-switcher for a 2 μm laser", *Optics Letters*, 37(3):395-397 (2012).

Xia et al., "Ultrafast graphene photodetector", *Nature Nanotechnology*, 4(12):839-843 (2009).

* cited by examiner

US 9,143,702 B2

LENS-FREE PLANAR IMAGER USING AN OPTICAL RESONATOR

CROSS-REFERENCE TO RELATED APPLICATIONS

This application is a continuation of International Application No. PCT/US2012/048833 filed Jul. 30, 2012, which is related to U.S. Provisional Application Ser. No. 61/513,826, filed Aug. 1, 2011, each of which is incorporated herein by reference in its entirety and from which priority is claimed.

STATEMENT OF FEDERALLY SPONSORED RESEARCH OR DEVELOPMENT

This invention was made with government support under Grant No. PECASE # FA9550-12-1-0045, awarded by the Air Force Office of Scientific Research. The government has certain rights in the invention.

BACKGROUND

The disclosed subject matter relates generally to techniques for lens-free super-resolution imaging.

The field of optical microscopy includes systems with imaging optics, e.g., series of lenses that project an object plane onto an imaging-plane which, in turn, is typically recorded by an imaging array such as a CCD camera or the retina. However, in some applications, it can desirable to acquire an image without the use of lenses. For example, limited-space applications such as endoscopy can benefit from small, lens-free imaging systems.

Electromagnetic waves, including those in the infrared, visual, and ultraviolet spectrum, propagating through a medium can undergo frequency-dependent effects known as dispersion. For example, light traveling through a prism can undergo phase velocity dispersion, wherein different frequencies of light are refracted differently (i.e., different wavelengths have different propagation velocities). The "dispersion relation" can describe the relation of wave properties, such as for example wavelength, frequency, velocity, and refractive index of a medium. Dispersion relations can depend on material composition of a medium through which an electromagnetic wave travels, the geometry of the medium, and other factors.

Photonic crystals (PCs) can have peculiar optical properties, which can allow for the modification and engineering of the dispersion relation of the crystal for photons at optical frequencies. Photonic crystals can be fabricated to affect the motion of photons. For example, nanoscale waveguides can be created by introducing defects in a periodic structure. Optical cavities can be created by removing one or more holes in a PC lattice. Such cavities can be high-Q and can have desirable modal volume. Additionally, optical cavities can be designed to include more than one mode localized in the cavity area. Such modes can be referred to as standing wave modes, which can be composed of superpositions of forward and backward traveling Bloch modes. Each standing wave can have a unique spatial distribution, which can correspond to a different resonant frequency for each mode.

SUMMARY

In one aspect of the disclosed subject matter, a method for lens-free imaging using optical resonator includes providing a series of standing waves, each wave indexed by a wave vector $k_i$. The optical resonator can have a predetermined dispersion relation describing a relationship between the standing waves and the corresponding wave vector. The intensity of the resonances corresponding to wavelengths of the standing waves can be measured. A magnitude and shift of the resonances corresponding to each of the standing waves can be measured. From this information, spatial information in k-space can be determined from the magnitude and shift for each resonance, which can be measured in frequency, and linked to the wave vector k using an inversion relationship. A spatial transform can be applied to the spatial information in k-space to generate an image.

In one embodiment, the series of standing waves can be provided in an optical cavity in a photonic crystal, and light can be coupled into the cavity through one or more waveguides. The light coupled into the cavity can be, for example, between 600 and 650 nm, and further can be spectrally filtered prior to coupling into the cavity.

In one embodiment, the photonic crystal can be contacted with a sample to be imaged, thereby creating a change in magnitude and shift of at least one of the resonance frequencies, linked via the dispersion relation to a wave vector. The intensity of the standing waves can be measured by transmitting light at corresponding wavelengths through an optical fiber to a photodetector. Alternatively, intensity can be measured remotely by detecting light leakage from the cavity. Additionally or alternatively, the photonic crystal can have some gain medium that generates light through photoluminescence or electroluminescence, providing an internal source of illumination. The leakage of this light from the photonic crystal, either vertically into free space or through an output waveguide, can be recorded to reconstruct the object.

In another aspect of the disclosed subject matter, a system for lens-free imaging can include an optical resonator adapted to contain a series of standing waves, each wave indexed by a wave vector $k_i$. The optical resonator can have a predetermined dispersion relation describing a relationship between the standing waves and the corresponding wave vector. A photodetector can be configured to measure the intensity of wavelengths corresponding to the standing waves. A processor can be electrically coupled to the photodetector and configured to determine, using the predetermined dispersion relation, a magnitude and shift of the wave vector k corresponding to each of the standing waves. The processor can be configured to determine spatial information in k-space from the magnitude and shift of the wave vector k corresponding to each of the standing waves using an inversion relationship. The processor can be configured to apply a transform to the spatial information in k-space to generate an image.

In one embodiment, the optical resonator can be an optical cavity in a photonic crystal. A light source and one or more waveguides can be adapted to couple light from the light source into the optical cavity. The optical resonator can be contacted with a sample, thereby causing a shift and amplitude modulation of at least one of the standing waves. The optical resonator can be a one, two, or three-dimensional optical resonator.

Figure 1:
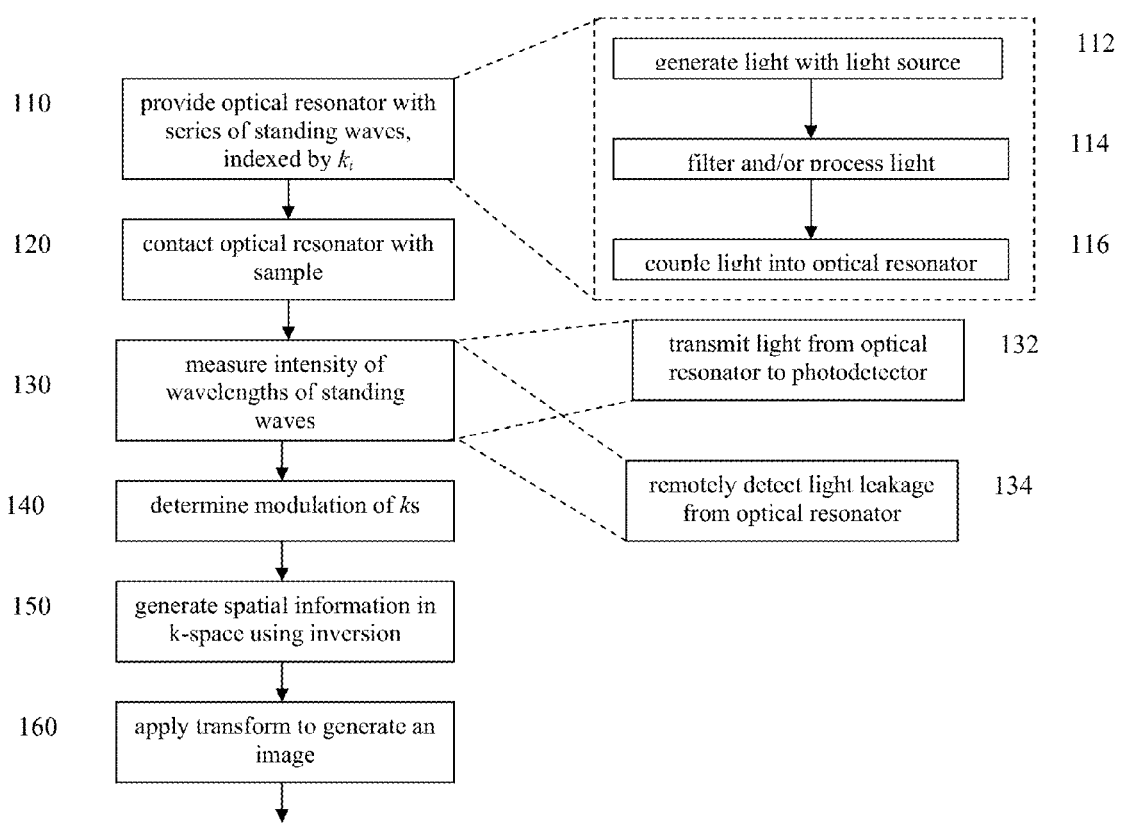
FIG. 1 is a flow diagram of a method for lens-free imaging in accordance with an embodiment of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

In one aspect of the disclosed subject matter, techniques for lens-free imaging include converting spatial information into spectral information using an optical resonator to set up a series of standing waves, which can be indexed by their longitudinal wave vectors k. A weakly absorbing specimen that interacts with the cavity field can modulate the standing waves through its refractive index and absorption, causing a shift and amplitude modulation in the modes with wave vectors k. Using the cavity medium's dispersion relation $\omega(k)$ that relates the light's frequency to the light's k-vector, this k-space modulation can be observed in the transmission spectrum of the cavity mode, given by $I(\omega)$. An inversion algorithm can be used to obtain the spatial information $\in(z)$ from the modulated cavity spectrum $I(\omega)$.

The dispersion relation of a photonic crystal can be given in terms of angular frequency by $\omega=2\pi f$ and wave number $k=290/\lambda$. Thus, a relationship between the dispersion relation $\omega(k)$ and the light's spatial frequency can be given by the dispersion relation, which can be computed for photonic crystals by numerical techniques such as finite difference time domain (FDTD) simulations.

Figure 5:
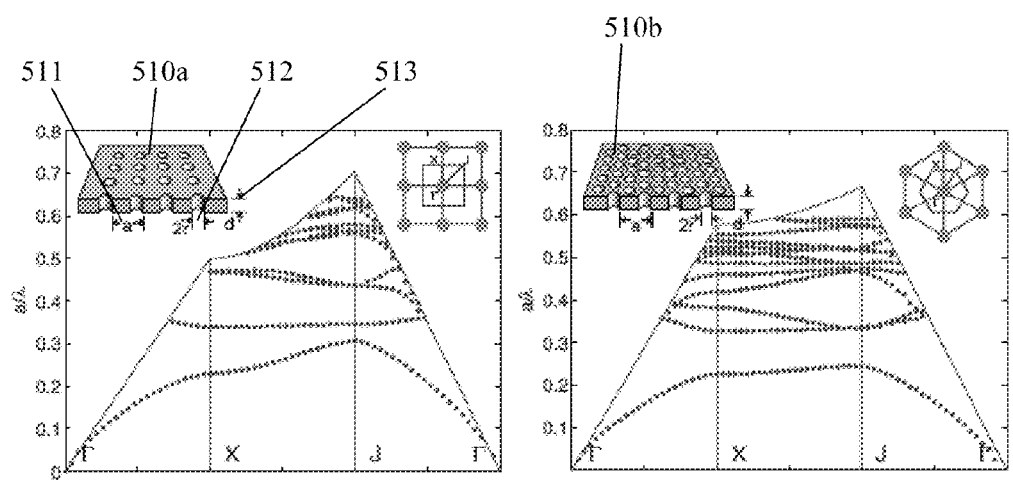
FIG. 5 illustrates the dispersion relation for a photonic crystal for use in lens-free imaging in accordance with an embodiment of the disclosed subject matter.
Figure 6:
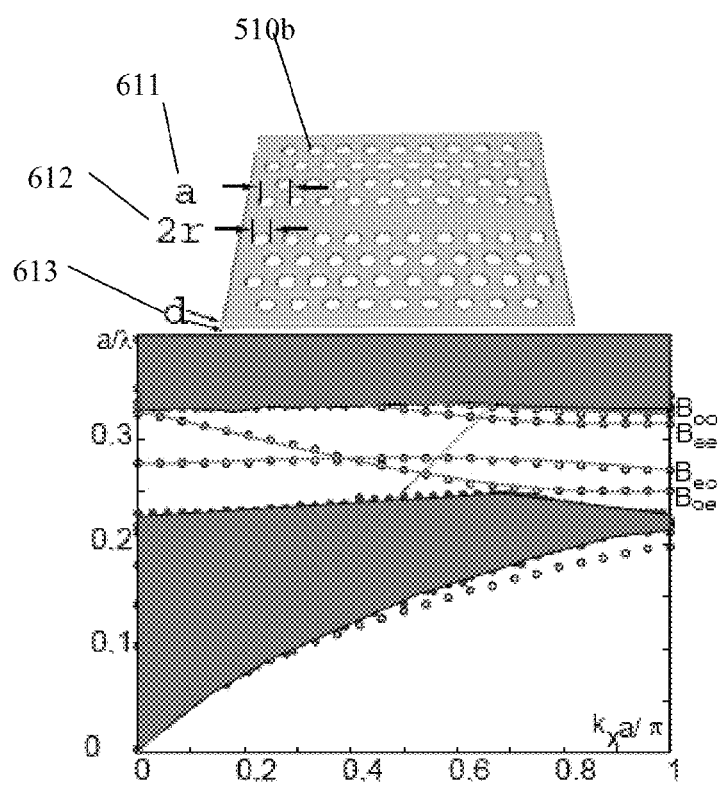
FIG. 6 illustrates the dispersion relation for a photonic crystal for use in lens-free imaging in accordance with anther embodiment of the disclosed subject matter.

For purposes of illustration, and not limitation, the dispersion relation characteristics of a photonic crystal will be described with reference to FIG. 5 and FIG. 6. A photonic crystal 510 can be fabricated by periodically modulating the refractive index of a thin semiconductor slab. The periodic modulation can result in a square lattice 510a or a hexagonal lattice 510b, or any other suitable lattice shape. The periodic modulation can introduce an energy band-structure for light in two dimensions. Cavity modes can be formed by introducing linear defects into a closed off portion of the lattice, e.g., by introducing mirrors to confine a portion of the mode of a waveguide. The lattice can have periodicity a 511 or 611, hole radius r 512 or 612, and slab thickness d 513 or 613. FIG. 5 depicts the TE-like mode band diagram for a square lattice 510a and hexagonal lattice 510b with r/a=0.4, d/a=0.55, and n=3.6. FIG. 6 depicts a plot of dispersion relation for a hexagonal waveguide formed in a hexagonal lattice 510b in the ΓJ direction, with r/a=0.3, d/a=0.65, and n=3.6.

The dispersion relation of each mode in an optical cavity can be sensitive to an index change in the cladding of the photonic crystal. Additionally, as disclosed herein, cavity modes in the photonic crystal bandgap medium can exhibit small group velocity, which can result in a nearly flat dispersion relation $\omega(k)$. That is, for example, a small range in frequency can correspond to a large range in k-vector. A large range in k-vectors can be important to map out both slowly varying and rapidly varying features of an image.

A small perturbation presented in the near field can cause the resonant modes of the cavity of the photonic crystal to respond differently, which can be presented by different resonant shifts corresponding to the position of the perturbation and/or amplitude modulation of the modes. As such and in accordance with the disclosed subject matter, a sub-wavelength feature can be mapped out by looking solely at k-space.

Particular embodiments of the method and system are described below, with reference to FIG. 1, and FIG. 2a, FIG. 2b, FIG. 2c (collectively, FIG. 2), for purposes of illustration, and not limitation. For purposes of clarity, the method and the system are described concurrently and in conjunction with each other.

An optical resonator 210 can be provided (110). The optical resonator 210 can be any suitable optical resonator. For example, in one embodiment, the optical resonator 210 can include two mirrors 211 reflective over a specified wavelength range given by the photonic crystal bandwidth, which can be controlled by the photonic crystal periodicity. Alternatively, the optical resonator 210 can include a photonic crystal 215 including a cavity 214. The photonic crystal 215 can include a periodic structure of linear defects 213 with a different dielectric constant. The photonic crystal can be fabricated from, for example, silicon. Alternatively, the photonic crystal can be fabricated from a polymer, such as Poly(methyl methacrylate) (PMMA).

The optical resonator 210 can be configured to resonate at a set of frequencies. That is, the optical resonator can have a plurality of standing waves. Each wave can be indexed by its wave vector, k. The standing waves can generated by generating (112) light with a list source 240. The light can then be filtered and/or processed (114) to achieve a desirable characteristic. For example, where the light source 240 emits broadband light, spectral filters can be utilized to filter the light to a narrow band.

Figure 2A:
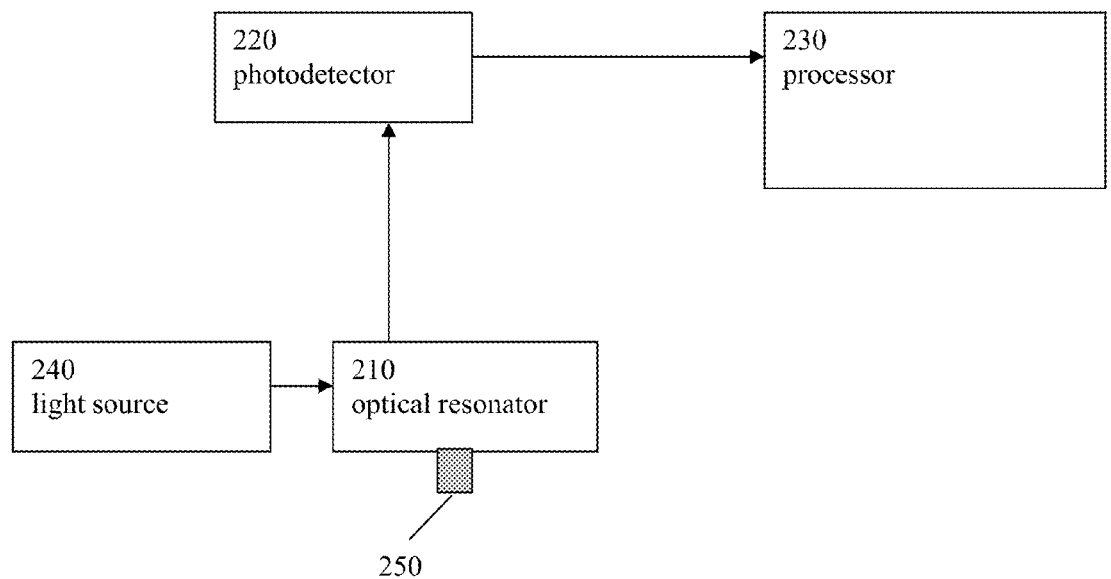
FIG. 2a is a block diagram of a system for lens-free imaging in accordance with an embodiment of the disclosed subject matter.
Figure 2B:
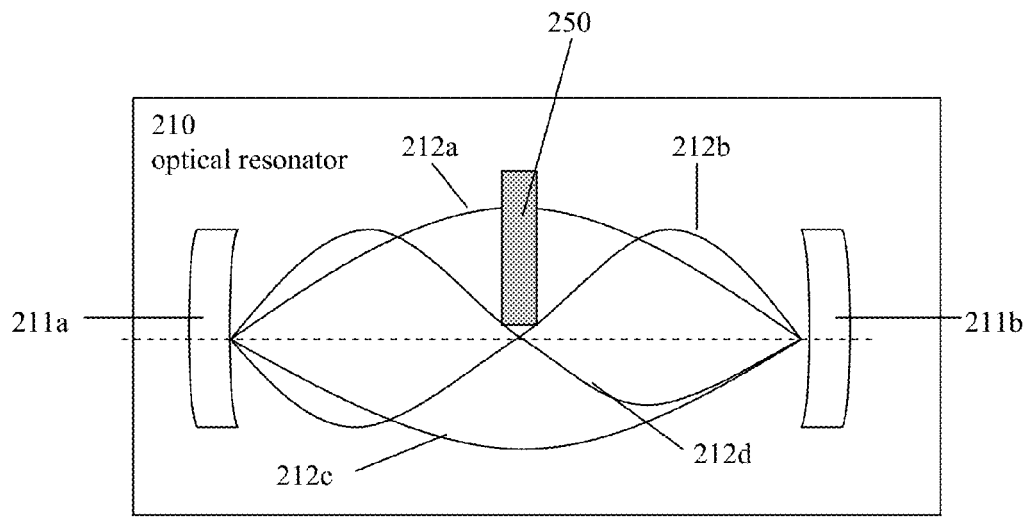
FIG. 2b is a diagrammatic representation of an optical resonator for lens-free imaging in accordance with an embodiment of the disclosed subject matter.
Figure 2C:
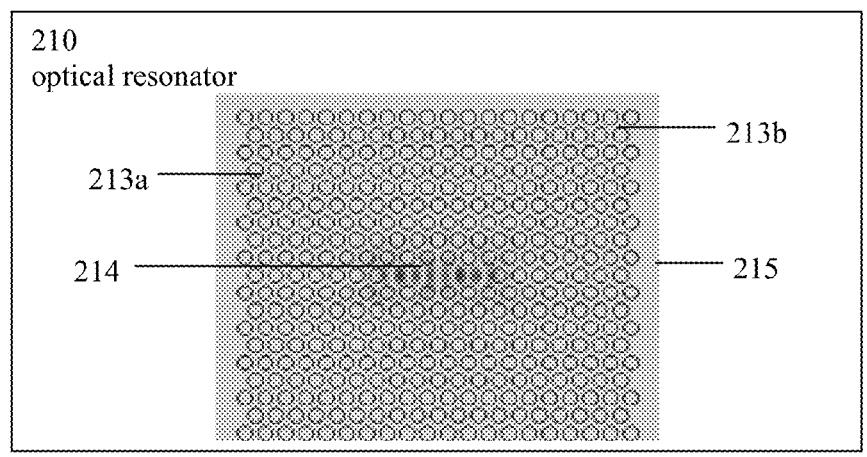
FIG. 2c is a diagrammatic representation of another optical resonator for lens-free imaging in accordance with an embodiment of the disclosed subject matter.

The light can then be coupled (116) into the optical resonator. For example, the light can be coupled (116) with the use of one or more waveguides. FIG. 2b provides an illustrative diagram of standing waves 212 in an optical resonator utilizing two reflective mirrors 211. The wavelength of the standing waves can be a multiple of the distance between the mirrors 211. For example, the fundamental mode 212a and 212c can have a wavelength of d/2, where d is the optical path (refractive index times distance) between the mirrors 211. The first mode 212b and 212d can have a wavelength of 2/4. Alternatively, the standing waves can correspond to characteristics of a cavity 214 in a photonic crystal 215.

The optical resonator 210 can have a predetermined dispersion relation. In many cases, it can be desirable to employ a flat dispersion relation w(k) because a large range of spatial frequencies {k} are thus encoded into a narrow frequency spectrum {w}. A narrow frequency spectrum can simplify the optical system. As an example, a triangular holey 2D photonic crystal lattice with lattice spacing α, defined in a high-index material such as Si, can have a bandgap from a/λ=0.25-0.3. This frequency range can then be used for creating localized defect states in the 2D lattice. Then, waveguide, cavity, or coupled-cavity modes can define the dispersion relation. The dispersion relation can be tailored through the hole size near the defect regions. The relation can be tailored in such a way as to ensure a one-to-one correspondence between resonance frequencies of standing modes and k-states that constitute these standing waves. As described herein, the dispersion relation can represent a relationship between the standing waves and their corresponding wave vector. The dispersion relation can be predetermined based on the characteristics of the optical resonator 210. For example, the geometry of the optical resonator and the refractive index of the medium in which it is contained can predetermine the dispersion relation. Moreover, where a photonic crystal is used as the optical resonator 210, the photonic crystal can be designed to result in a desired dispersion relation.

In one embodiment, the photonic crystal can be designed to achieve a relatively flat dispersion relation, i.e., the derivative of the frequency w with respect to k is small. A value of dw/dk~0.01-0.1 c can be suitable, where c is the speed of light. That is, the cavity 214 of the photonic crystal 215 can be designed so that resonant modes can have small group velocity, whereby a small range in frequency corresponds to a large range in k.

The optical resonator 210 can be contacted (120) with a sample 250. The position of the sample relative to the cavity can result in the perturbation and shift of resonance of difference modes. The techniques disclosed herein can, for example, map the change of index $\Delta\epsilon(\vec{r}) = \Delta\epsilon_{real}(\vec{r}) + i \cdot \Delta\epsilon_{image}(\vec{r})$ in space using Fourier transform for a small object present at the cavity region. The existence of small perturbation can result in a shift of resonance for each mode and an additional material loss, which can correspond to the broadening of quality factor Q. This relationship can be expressed, for example, using first order perturbation theory:

$$\frac{\Delta\omega_m}{\omega_m} \approx -\frac{1}{2} \frac{\int_V \Delta\varepsilon_{real,m} |E_m(\vec{r})|^2 \, d\vec{r}}{\int_V \varepsilon_0 |E_m(\vec{r})|^2 \, d\vec{r}}, \quad (1)$$

where $\epsilon_0$ is the dielectric constant of the cavity material, $\Delta\epsilon$ is the difference of the dielectric constant of the surrounding of the cavity with respect to the gas or liquid surrounding the cavity, and $\epsilon$ can be a function of position, r.

Thus, a resonance shift of each mode can be calculated. For perturbation in a relatively small size, the shift of resonance for a particular mode m, $\Delta\omega_m$ can depend on where it sits in the electric field of a mode m, $E_m(r)$. $\Delta\epsilon_m$ can be obtained so as to deduce the change in electrical permittivity by, for example, deducing from Q factor using the relationship:

$$\frac{1}{Q_{mat,m}} = \frac{1}{Q_{ptrb,m}} - \frac{1}{Q_{0,m}}, \quad (2)$$

where $Q_{0,m}$ is the original Q factor for mode m and can drop to $Q_{ptrb,m}$ with the presence of the small perturbation, which can introduce extra extrinsic loss denoted by the absorption coefficient $\alpha_{mat,m}$ as follows:

$$Q_{mat,m} = \frac{2\pi n_{pc}}{\alpha_{mat,m} \lambda_m} \quad (3)$$

The absorption coefficient $\alpha_{mat,m} = \gamma_{mat,m}/(c/n_{pc})$, and thus:

$$\gamma_{mat,m} = \omega_m \left( \frac{1}{Q_{ptrb,m}} - \frac{1}{Q_{0,m}} \right)^{-1} \quad (4)$$

The change in the imaginary part of $\Delta\epsilon_i(k)$ can be obtained by substituting equation 4 into equation 1:

$$\gamma_{mat,m} \approx -\frac{1}{2} \frac{\int_V \Delta\varepsilon_{imag,m} |E_m(\vec{r})|^2 \, d\vec{r}}{\int_V \varepsilon_0 |E_m(\vec{r})|^2 \, d\vec{r}}. \quad (5)$$

Given the change in the complex electrical permittivity $\Delta\epsilon$ in k-space, a Fourier transform can be used to obtain $\Delta\epsilon(\vec{r})$:

$$\Delta\varepsilon(\vec{r}) = \sum_m \Delta\varepsilon(\vec{k}_m) \exp(-i\vec{k}_m \cdot \vec{r}) = \quad (6)$$

$$\sum_m \left[ \Delta\varepsilon_{real,m}(\vec{k}_m) + i \cdot \Delta\varepsilon_{imag,m}(\vec{k}_m) \right] \exp(-i\vec{k}_m \cdot \vec{r}).$$

The intensity of wavelengths corresponding to the standing waves can be measured (130). In one embodiment, the optical resonator 210 can be coupled to a photodetector 220 via one or more waveguides. The waveguides can be, for example, a photonic crystal with a pathway defined therein to guide (132) light from the optical resonator 210 to the photodetector 220. Additionally or alternatively, light can be guided from the optical resonator 210 using one or more optical fibers. The fibers can be, for example, single mode fibers. Alternatively, the photodetector 220 can be adapted to receive light remotely (134) from light leakage from the optical resonator 210.

The intensity spectrum of the optical cavity 210 can be converted (140) into k-space using the dispersion relation, which can be deduced a-priori from numerical or analytical calculations. That is, a magnitude and shift of the wave vector k corresponding to each standing wave can be determined.

Spatial information, in k-space, can then be determined (150) based on the magnitude and shift of the wave vector k corresponding to each standing wave using an inversion relationship. The inversion relationship is given by the dispersion relation ω(k). To simplify the inversion, ω(k) can be single-valued, i.e., there exists unique pairs between a spatial frequency k (or −k) and ω(k).

A transform can then be applied (160) to the spatial information in k-space to generate an image. In one embodiment, for example, the transform can be a fast Fourier transform. Each wave vector k can correspond to a coefficient in the fast Fourier transform. That is, each wave vector k can represent a phase (i.e., the resonant shift of the standing waves in the optical resonator 215) and a magnitude (i.e., the amplitude of each standing wave in the optical resonator 215). The transform can be given by the relationship $$I(r) = c_0 \sum_{k=-\infty}^{\infty} e^{-ik*r} I(k),$$

where $c_0$ is a proportionality factor that is unimportant in this step.

The techniques disclosed herein can be employed in one, two, or three dimensions. For purposes of illustration, and not limitation, exemplary one dimensional imaging techniques will now be described.

Figure 3:
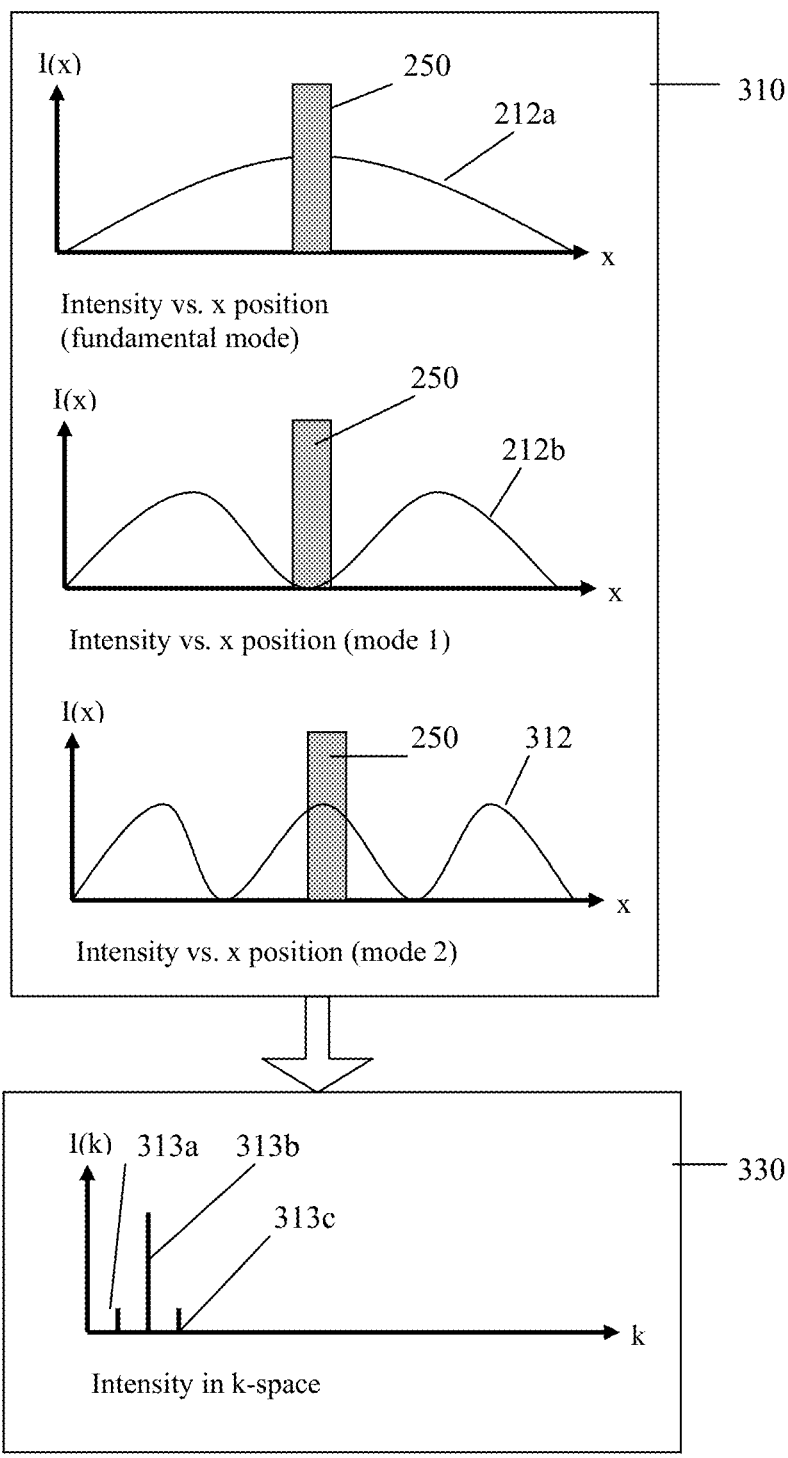
FIG. 3 illustrates imaging a sample in accordance with an embodiment of the disclosed subject matter.

With reference to FIG. 3, a series of standing waves (212a, 212b and 312) can be set up in an optical resonator. A sample 250 can be contacted with the optical resonator at a location along the resonators axis (x). FIG. 3 includes a schematic representation 310 of intensity of the standing waves vs. position along the resonator axis. The sample 250 can be an emitter or an absorber. That is, for example, light in the cavity can interact with the sample 250 when it is contacted with a surface of the cavity. Additionally or alternatively, the sample 250 can have a refractive index different from that of the cavity medium, such that the light in the cavity can be modulated based on the sample's 250 refractive index. In this manner, certain standing waves can be modulated differently depending on the position of the sample 250.

For example, where the resonator has three standing waves including the fundamental mode 212a, the first mode 212b, and the second mode 312, the sample can be placed in the middle of the resonator. The sample 250 can absorb (or emit) some light at the fundamental wavelength 212a and the second wavelength 312. However, the sample 250 can fail to interact with the first mode 212b.

The intensity of the standing waves (212a, 212b, and 312) can be detected in accordance with the disclosed subject matter and converted into k-space. FIG. 3 depicts a graph 330 of intensity in k-space vs wave vector k index. That is, the first wave vector 313a corresponding to the fundamental mode 212a has a low intensity due to interaction with the sample 250. The second wave vector 313b has a high intensity due to the lack of interaction with the sample 250. The third wave vector 313c has a low intensity due to interaction with the sample. In this manner, spatial information has been encoded intro spectral information. The k-space information can then be converted into spatial information using an inversion algorithm, and the spatial k-space information can be converted into an image by applying a transform.

Figure 4A:
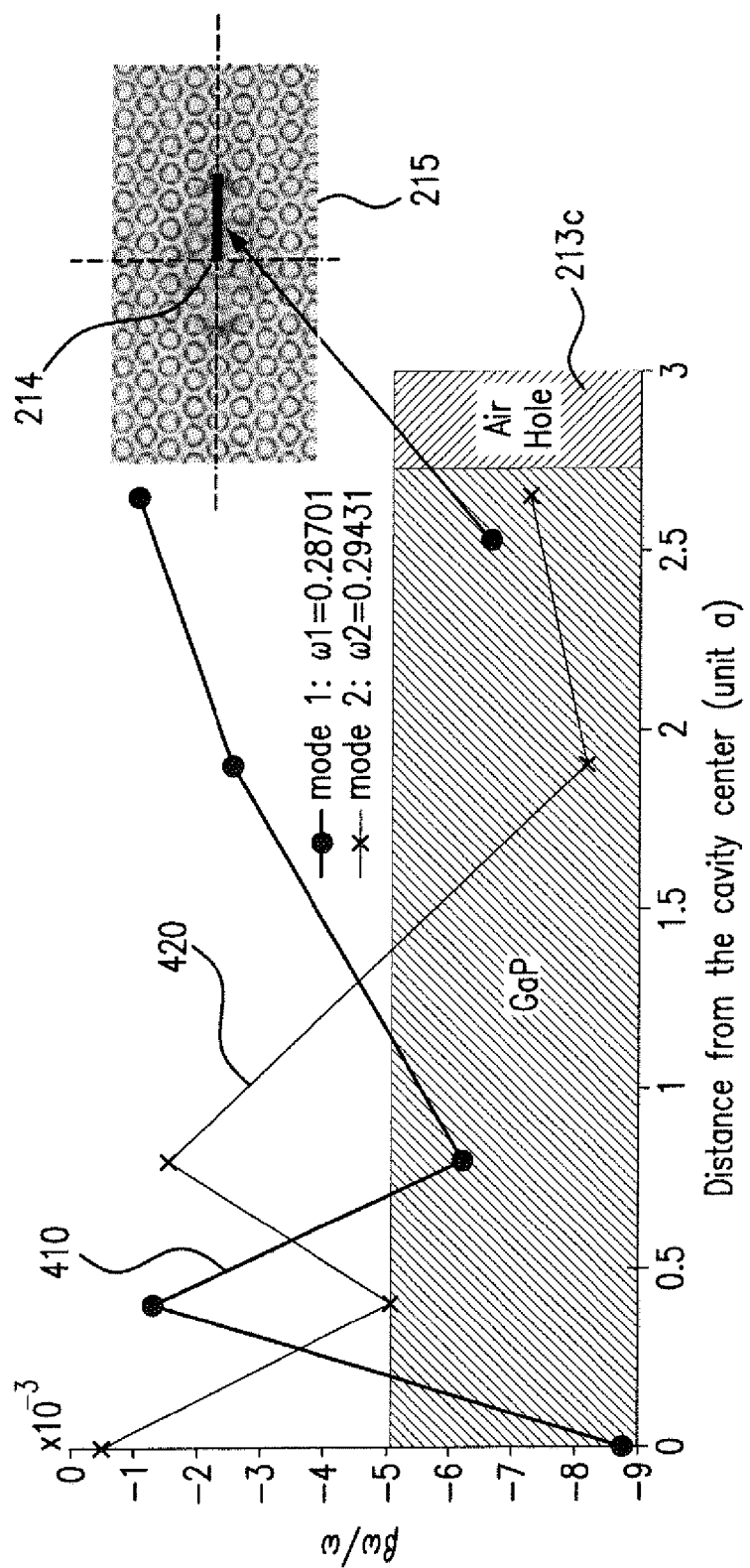
FIG. 4a illustrates imaging a sample in accordance with another embodiment of the disclosed subject matter.
Figure 4B:
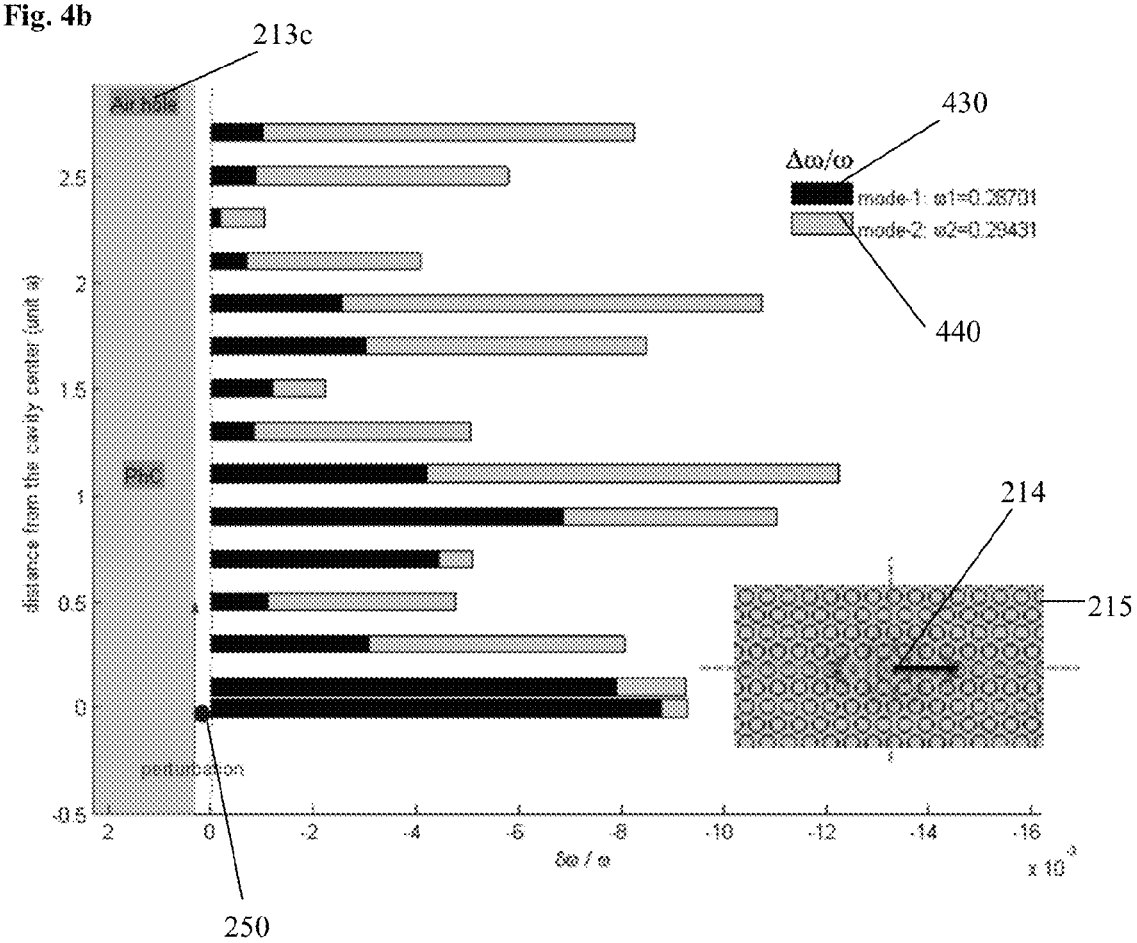
FIG. 4b illustrates the intensity of standing waves of an optical resonator into k-space in accordance with an embodiment of the disclosed subject matter.

With reference to FIGS. 4a and 4b, a cavity 214 in a photonic crystal 215 can have two even modes. The cavity 214 can exist by virtue of having 5 missing holes in the photonic crystal 215. The two modes 410 and 420 can have different spatial distributions. According to equation 1, when the perturbation due to a sample 250 sits at some spot where mode 1 has maximum intensity while mode 2 has minimum intensity, they can exhibit different resonant shifts. Due to the strong nonlinear dispersion relation of the photonic crystal 215, a small shift in frequency domain can be amplified in the spatial domain. FIG. 4a illustrates resonance shifts of the two modes 410 and 420 corresponding to the position of a perturbation (illustrated as at the center of the cavity 214). FIG. 4b illustrates resonance shifts of the two modes 430 and 440 in k-space.

Because spatial information is converted into spectral information in accordance with the disclosed subject matter, an entire image can be automatically encoded in the spectrum, as in dense wavelength division multiplexing (DWDM). The image can thus be transmitted through a single mode waveguide, such as optical fiber. This feature can enable applications such as endoscopy with an ultra-small 2D planar PC imager (a 100 nm thick, microns wide sheet) coupled to a single mode optical fiber. Furthermore, images can be acquired remotely by light leakage from the photonic crystal: for instance, the photonic crystal can be embedded in a tissue. Upon optical excitation, it can emit the image of its local environment in the spectral domain, which can be recorded from outside the tissue, even in a diffusive medium.

Figure 7:
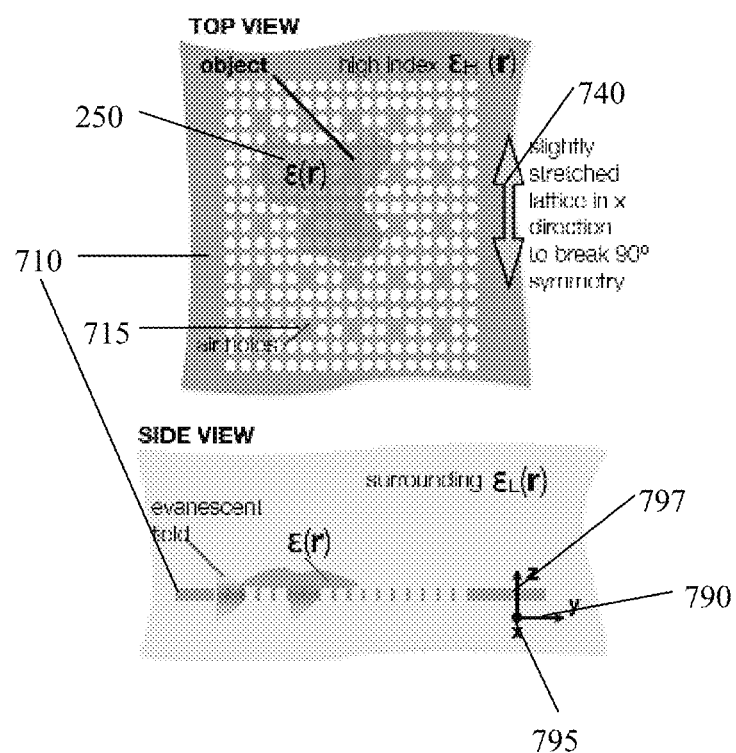
FIG. 7 is a schematic representation of an optical resonator for use in two-dimensional lens-free imaging in accordance with an embodiment of the disclosed subject matter.
Figure 8:
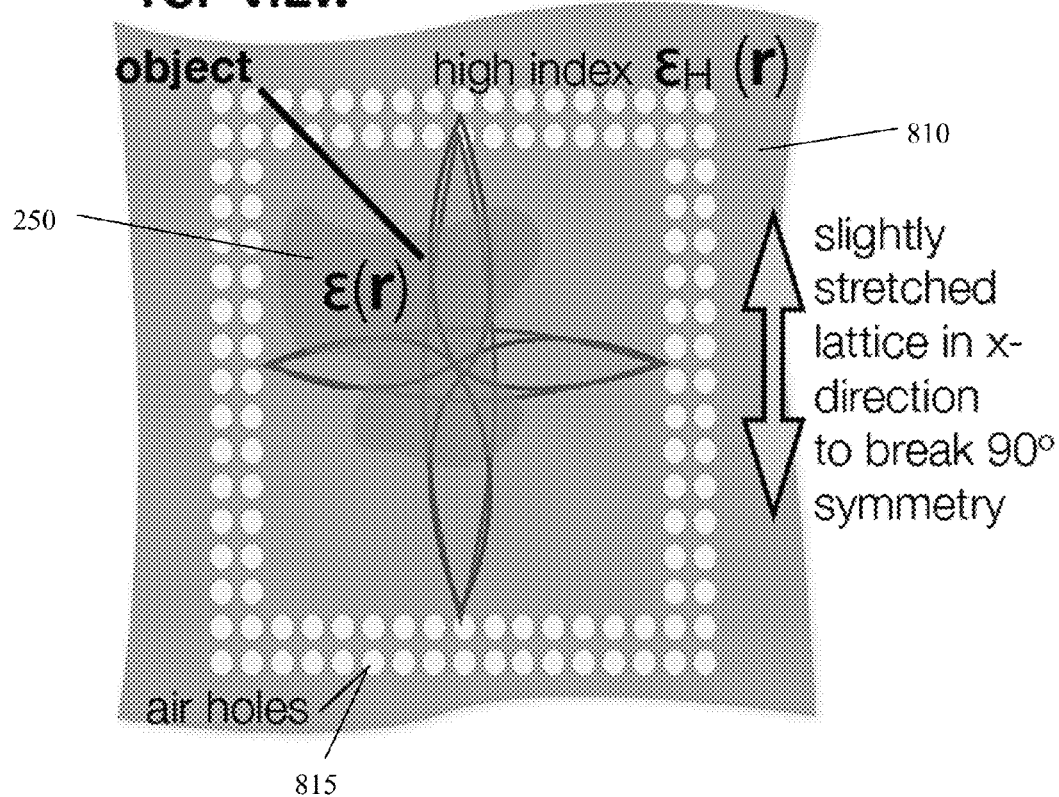
FIG. 8 is a schematic representation of an optical resonator for use in two-dimensional lens-free imaging in accordance with another embodiment of the disclosed subject matter.

In one embodiment, and with reference to FIG. 7 and FIG. 8 techniques for two dimensional lens-free imaging can include using a number of standing waves in x 795 and y 790 dimensions that have unique frequencies. For example, photonic crystal 2D coupled resonator array (PCCRA) 710 can be used. When the defects 715 within the array 710 are close enough together such that the defect modes overlap with the nearby cavity, some of the defect modes can be come coupled and a band forms. These bands can be described by a dispersion relation w(k), similar to that depicted in FIG. 6, where k is the wave vector in the x 795, y 790 plane, the z 797 axis being normal to the surface of the photonic crystal. Different lattice geometries can be used, including for example a square, triangular, or hexagonal lattice.

For purposes of illustration and not limitation, a square lattice 710 with single hole defects can be provided. The frequencies of standing waves with 90 degree rotated standing waves can be equal due to the 90 degree lattice symmetry. Such an equality can create an ambiguity in image reconstruction owing to the lack of unique relationship between the frequency w and wave vector k. In some embodiments, the degeneracy of these standing waves can be broken by, for example, changing the lattice spacing in the x and y directions to shift the resonance frequencies by approximately a cavity line width. For example, the photonic crystal can be stretched 740 along one axis by approximately 1% to approximately 2%.

In another embodiment, rather than a PCCRA, a 2d Fabry cavity 810 can be used, in which light can be configured within a 2D cavity bounded by defects to create a mirror 815. In this embodiment, standing waves with low frequency can fall outside the reflection band of the mirror 815 surrounding it. In certain embodiment, the mirror 815 can be a photonic crystal mirror, any other suitable type of dielectric mirror, or a metal mirror.

In like manner, techniques for three-dimensional lens-free imaging can include the use of a thee dimensional photonic crystal. Alternatively, a three dimensional open cavity can be employed. Degeneracy of the standing wave frequencies can be broken by slight asymmetries.

The ability to use DWDM recording equipment according to the presently disclosed techniques can lower costs and allow the entire system to be integrated in photonic integrated chips. 1D and 2D systems devices can be manufactured in a massively parallel fashion using previous generation optical lithography processing. Such optical lithography can project a mask onto a photosensitive film on the Si membrane sample to produce a copy. This copy can then be etched using a reactive ion plasma into the target sample, producing a photonic crystal pattern. A wet chemical etch can release a sacrificial layer underneath the Si membrane to release it from the substrate. The sacrificial layer can be, for example $SiO_2$ for Silicon on Insulator wafers. Additionally, systems in accordance with the disclose subject matter can be used in a passive mode in which external light can be coupled into cavity modes. Alternatively, systems in accordance with the disclosed subject matter can be fabricated from light emitting material (e.g., III/V semiconductor materials), in which case an external pump beam can be used to internally illuminate standing waves in the device. Further, the system in accordance with the disclosed subject matter can be electrically pumped, removing the need for external illumination.

The resolution of an imaging system in accordance with the subject matter disclosed herein can be given by the smallest feature size of the standing wave, which can be below 50 nm.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

The invention claimed is:

1. A method for lens-free imaging using an optical resonator, comprising:
   providing a series of standing waves, each wave indexed by a wave vector $k_i$, the optical resonator having a predetermined dispersion relation describing a relationship between the standing waves and the corresponding wave vector;
   contacting the optical resonator with a sample to be imaged, thereby creating a change in the magnitude and shift of at least one of the wave vectors;
   measuring the intensity of wavelengths corresponding to the standing waves;
   determining, using the predetermined dispersion relation, a magnitude and shift of the wave vector k corresponding to each of the standing waves;
   determining spatial information in k-space from the magnitude and shift of the wave vector k corresponding to each of the standing waves using an inversion relationship; and
   applying a transform to the spatial information in k-space to generate an image.

2. The method of claim 1, wherein the series of standing waves are provided in an optical cavity in a photonic crystal, and where providing further comprises coupling light through at least one waveguide into the cavity.

3. The method of claim 1, wherein coupling the light through at least one waveguide further comprises directing the light through one or more spectral filters.

4. The method of claim 1, wherein the light is between 600 and 650 nm.

5. The method of claim 1, wherein the sample is an absorbing sample with a refractive index different than a refractive index of the photonic crystal, and wherein determining the magnitude and shift of the wave vector k corresponding to each of the standing waves further comprises determining a shift and amplitude modulation based on a perturbation of the standing waves from the refractive index and an absorption characteristic of the sample.

6. The method of claim 1, wherein the sample further comprises an emitter, whereby an emission of the emitter interacts with the standing waves of the optical cavity.

7. The method of claim 1, wherein measuring the intensity of wavelengths further comprises transmitting the wavelengths through an optical fiber to a photodetector.

8. The method of claim 1, wherein measuring the intensity of wavelengths further comprises measuring the intensity of wavelengths remotely by a light leakage from the photonic crystal.

9. The method of claim 1, wherein the providing further comprises providing a multi-dimensional optical resonator with a series of standing waves in each dimension.

10. A system for lens-free imaging, comprising:
    an optical resonator adapted to contain a series of standing waves, each wave indexed by a wave vector $k_i$, the optical resonator having a predetermined dispersion relation describing a relationship between the standing waves and the corresponding wave vector;
    a photodetector configured to measure the intensity of wavelengths corresponding to the standing waves; and
    a processor, electrically coupled to the photodetector, configured to determine, using the predetermined dispersion relation, a magnitude and shift of the wave vector k corresponding to each of the standing waves resulting from contacting the optical resonator with a sample to be imaged, configured to determine spatial information in k-space from the magnitude and shift of the wave vector k corresponding to each of the standing waves using an inversion relationship, and configured to apply a transform to the spatial information in k-space to generate an image.

11. The system of claim 10, wherein the optical resonator is an optical cavity in a photonic crystal, further comprising:
    a light source;
    at least one waveguide for coupling light from the light source into the optical cavity.

12. The system of claim 10, wherein the sample is an absorbing sample with a refractive index different than a refractive index of the optical resonator, and wherein the processor is further configured to determine the magnitude and shift of the wave vector k corresponding to each of the standing waves using a shift and amplitude modulation based on a perturbation of the standing waves from the refractive index and an absorption characteristic of the sample.

13. The system of claim 10, further comprising an optical fiber, optically coupled to the optical resonator and the photodetector, for transmitting the wavelengths corresponding to the standing waves.

14. The system of claim 10, wherein the photodetector is configured to measure the intensity of wavelengths corresponding to the standing waves remotely by detecting a light leakage from the optical resonator.

15. The system of claim 10, wherein the optical resonator further comprises a multi-dimensional optical resonator.

* * * * *